(12) United States Patent
Benderev

(10) Patent No.: US 6,302,840 B1
(45) Date of Patent: Oct. 16, 2001

(54) SURGICAL MONITOR

(76) Inventor: Theodore V. Benderev, 26975 Magnolia Ct., Laguna Hills, CA (US) 92653

( * ) Notice: Subject to any disclaimer, the term of this patent is extended or adjusted under 35 U.S.C. 154(b) by 0 days.

(21) Appl. No.: 09/511,822

(22) Filed: Feb. 24, 2000

Related U.S. Application Data

(63) Continuation-in-part of application No. 09/157,466, filed on Sep. 21, 1998, now Pat. No. 6,050,937.

(51) Int. Cl.$^7$ .............................. A61F 2/00; A61F 13/00
(52) U.S. Cl. ............................................. 600/37
(58) Field of Search .................. 600/37, 30, 561, 600/29, 547, 31, 485–488, 587, 591; 128/855, 898; 607/105

(56) References Cited

U.S. PATENT DOCUMENTS

| | | | |
|---|---|---|---|
| 5,518,504 | * | 5/1996 | Polyak .................................. 600/31 |
| 6,056,699 | * | 5/2000 | Sohn et al. ........................... 600/561 |
| 6,117,067 | * | 9/2000 | Gil-Vernet ............................. 600/30 |
| 6,135,945 | * | 10/2000 | Sultan .................................. 600/30 |

OTHER PUBLICATIONS

"AMS Sphincter 800 Urinary Prosthesis" American Medical Systems/1993/2 Pages.
"Atlas of Transvaginal Surgery" W.B. Saunders/Surgical Therapy for Urinary Incontinence/7 Pages.
"Treatment of Remale Incontinence Secondary to Urethral Damage or Lass" by Jerry G. Blaivas, MD/Evaluation and Treatment of Urinary Incontinence/May 1991/9 Pages.

"Successful Pubovaginal Sling Surgery" by Jerry G. Blaivas, MD/Contemporary Urology/2 Pages.

* cited by examiner

Primary Examiner—John P. Lacyk
Assistant Examiner—Brian Szmal
(74) Attorney, Agent, or Firm—Stetina Brunda et al.

(57) ABSTRACT

A system and method for measuring and indicating the degree of tension and/or positioning of a surgical sling, in particular, a suburethral sling, during surgery. In a first embodiment, the invention comprises a sensor interposable between a suburethral sling and the urethra supported thereby for measuring either relative spatial positioning and/or pressure. A monitor is provided for providing an indication when such tension/pressure/spacing attains optimal levels that correlate with ideal surgical outcomes. In a second embodiment, the invention comprises a tension monitor that may be connected, via a suture, to either respect one or both ends of a suburethral sling. The device may be utilized to manipulate the tension in or positioning of such sling to enable the surgeon to secure such sling in a manner that causes the sling to maintain a desired tension and/or imparted desired urethral support.

15 Claims, 3 Drawing Sheets

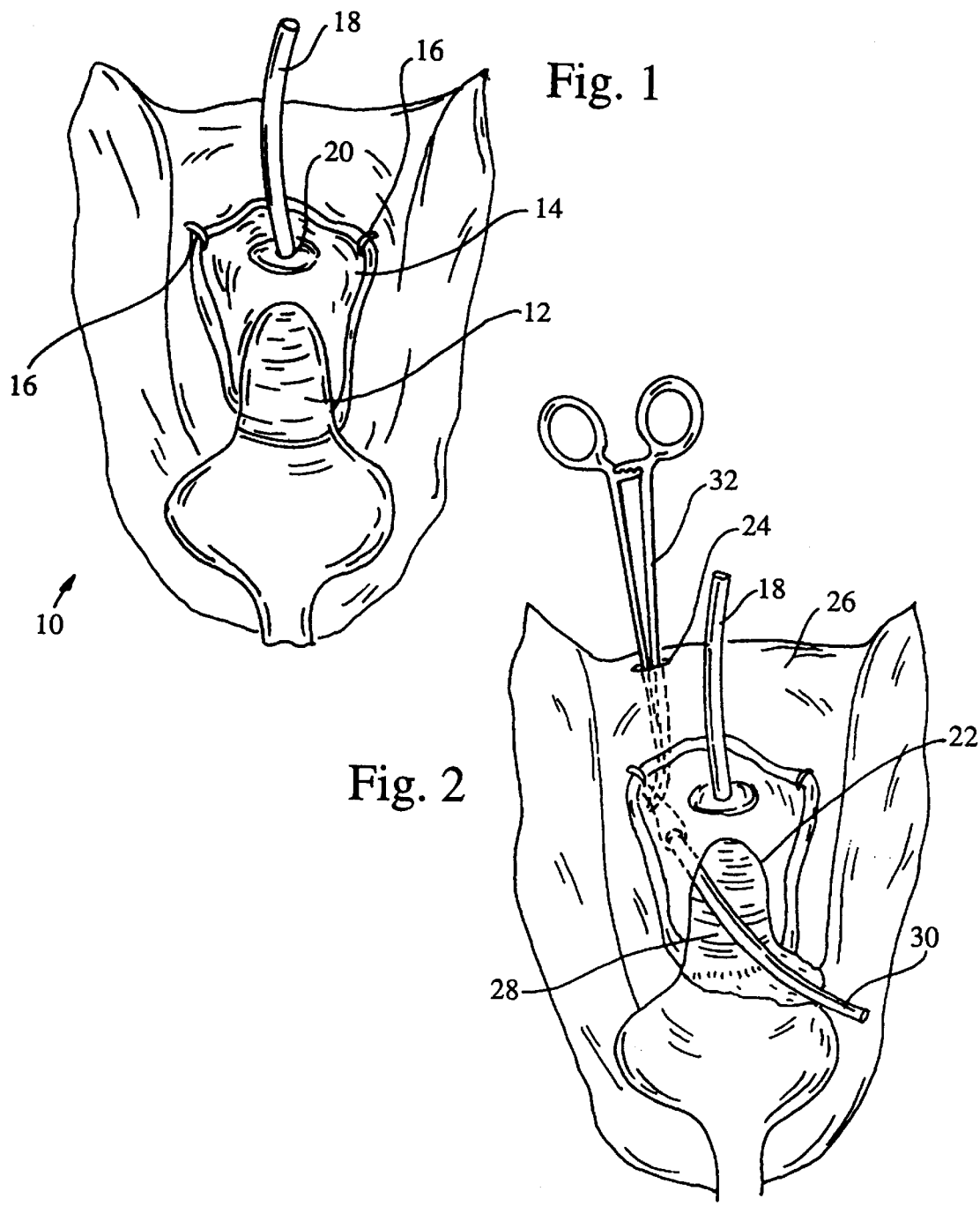

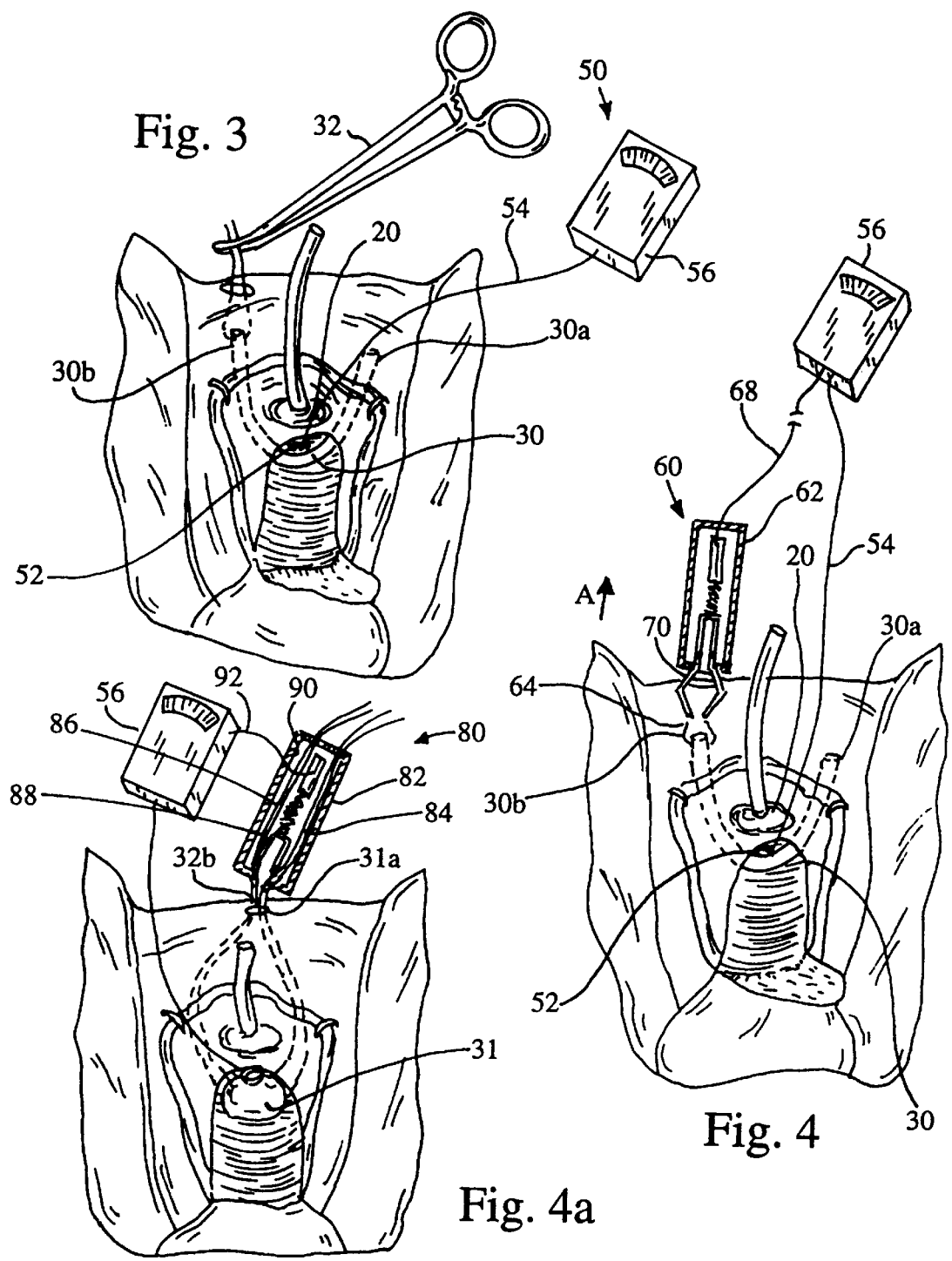

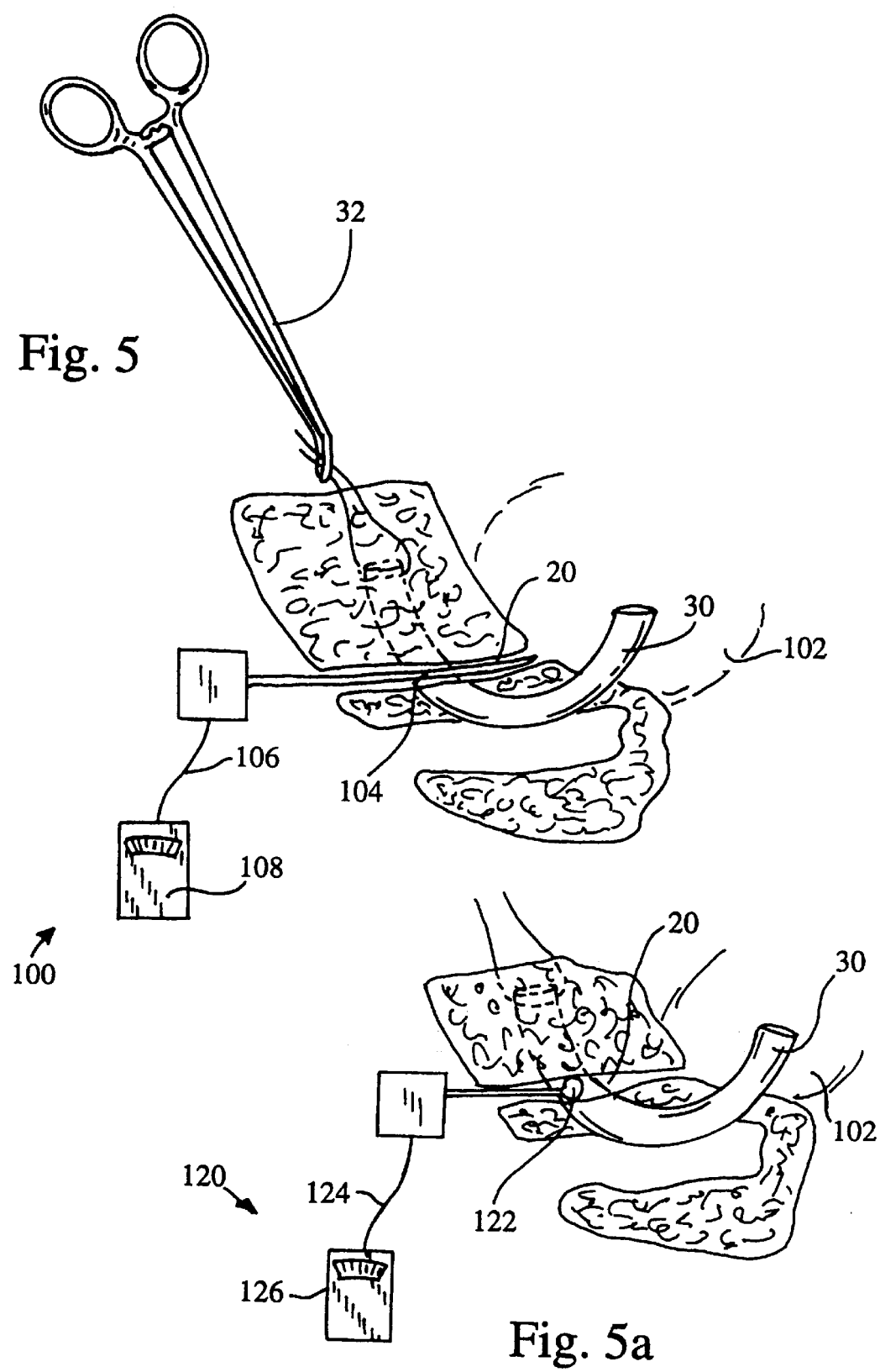

SURGICAL MONITOR

The present application is a continuation-in-part of patent application Ser. No. 09/157,466 filed Sep. 21, 1998, now U.S. Pat. No. 6,050,937, now in the issuance process, and likewise relies on the disclosure provided for in Disclosure Document No. 437,730, having a date of receipt of Jun. 15, 1998.

BACKGROUND OF THE INVENTION

Urinary incontinence is believed to affect 15% to 30% of non-institutionalized persons over the age of 60, and more than 50% of elderly persons (over the age of 60) who reside in nursing homes. The presently available modes for the treatment of urinary incontinence fall into four general categories, namely: (i) management apparatus; (ii) behavioral; (iii) pharmacologic; and (iv) surgical.

With respect to the latter, numerous procedures and devices utilized therewith are available to treat urinary incontinence of a variety of etiologies in men, women and children. Among the well-recognized procedures include the use of fluid-filled urinary prostheses which typically comprise a cuff pump and pressure regulating balloon. Exemplary of such devices is the AMS Sphincter 800™, produced by American Medical Systems. Typically, such device is implanted in either the bulbus urethra or bladder neck in men and adolescent males. In females, the cuff portion of such device is placed at the bladder neck.

The cuff of the urinary prostheses, which is filled with fluid, surrounds the urethra and gently squeezes it closed to keep urine in the bladder. To urinate, the cuff is deflated by squeezing the pump several times, which causes the fluid to move from the cuff to the balloon member. Within several minutes after urinating, the fluid atomically flows from the balloon back to the cuff, and as a consequence, causes the latter to become full and squeeze the urethra closed, thus restoring continence once again.

While effective in controlling urinary incontinence, such urinary protheses suffer from numerous drawbacks. In this regard, such urinary protheses are difficult and embarrassing to operate. Moreover, such urinary prostheses are not ideally suited for all types of urinary incontinence, are contraindicated in a variety of patients, and are associated with complications, such as excessive cuff pressure.

An alternative and well-recognized surgical procedure available for those suffering urinary incontinence, and particularly women, is suburethral sling surgery. The specifics regarding such surgical procedure are disclosed in greater detail in the following references: Blaivas, Jerry, G. *Successful Pubovaginal Sling Surgery, Contemporary Urology*, JulY, 1993; Blaivas, Jerry G., *Treatment of Female Incontinence Secondary To Urethral Damage Or Loss*, Urologic Clinics of North America, Vol. 18, No. 2, May, 1991; Raz, Schlomo, *Surgical Therapy For Urinary Incontinence, Atlas Of Transvaginal Surgery*, the teachings of which are expressly incorporated herein by reference.

Essentially, such surgical procedure involves the formation of a sling, which may comprise a harvested graft from a donor, of the patient's own tissue or an elongate strip fabricated from synthetic material, that is selectively positioned beneath the urethra and secured above or to the abdominal fascia. Alternatively, the opposed ends of the sling may be fixed in place, via a suture and anchored to the pubic bone of the patient or in various other ways such as to sutures or tissue adjacent to the urethra.

While suburethral sling surgery, which includes pubovaginal sling surgery, is considered the procedure of choice for women with urinary incontinence resulting from intrinsic sphincter deficiency (ISD), also referenced as type III stress urinary incontinence, to date, however, such procedure has not achieved widespread popularity. In this regard, although such surgical procedure reportedly has a success rate consistently above over 80%, efforts to popularize this durable technique for all forms of stress incontinence have been hampered by the significant post-operative complications that can arise in those situations where suburethral sling surgery is performed incorrectly. The most common complication of surgical procedure is caused from placing too much tension on the sling at the time of surgery, which as a consequence causes urinary retention, detrusor instability, or both.

While attempts have been made to provide surgeons with means to properly set the accurate tension within a sling during suburethral sling surgery, such devices have met with limited success. The most well known of such devices include spacers, the latter typically comprising a small spherical body mounted upon the pubic bone of the patient. Spacers typically have a channel formed therein which provides the surgeon with a surface upon which sutures of the free end of the sling may be affixed. While generally effective in providing the surgeon with any indication as to the degree of tension in the sling, let alone what impact the position of the sling has with respect to anatomical positioning of and pressure within the urethra.

Further prior art systems and procedures, such as ultrasound, lateral cystourethrography, and the Q-tip test, while generally effective in measuring the urethral angle, an important factor in evaluating incontinence surgery, are poorly adapted in providing the surgeon with any kind of indication as to the proper position of and pressure within the urethra during the actual suburethral sling surgery. Among the references discussing such systems include Schaer, G.N. et al., *Perineal Ultrasound for Evaluating the Bladder Neck and Urinary Stress Incontinence*, Obstet. Gynecol., February 1995; 85(2): 220–4; and Bergman, A., et al., *Negative Q-tip Test as a Risk Factor for Failed Incontinence Surgery in Woman*, J. Reprod. Med. March 1989; 34(3): 193–7.

Notwithstanding the fact that excessive sling tension has been identified as the major cause for complications in suburethral sling surgery and that crude attempts have been made to address the same, there presently does not exist any system or procedure by which the surgeon performing such operation can quantify during the operation the amount of tension or pressure being imparted by the sling to the urethra. There is further lacking in the art a system and method that, in addition to identifying the amount of tension or pressure imparted by a suburethral sling upon the urethra also provides an indication as to the optimal degree of tension to be imparted by the sling in supporting the urethra, as well as when such optimal amount of tension is attained. Still further, there exists a need in the art for systems and methods that enable the surgeon performing a suburethral sling surgery to identify the proper position of and pressure within the urethra of the patient so that the resultant sling imparts an optimal tension, and hence the desired degree of structural stability to the urethra supported thereby.

SUMMARY OF THE INVENTION

The present invention specifically addresses and alleviates the above-identified deficiencies in the art. In this regard, the present invention is directed to systems and methods for measuring and identifying the tension of a suburethral sling, as well as measure the pressure exerted thereby upon the urethra during a suburethral sling surgical procedure. The present invention is further directed to systems and methods that provide a surgeon performing a suburethral sling procedure with an indication as to the optimal degree of tension or spatial relationship a sling possesses relative the urethra of a particular patient undergoing such procedure, as well as systems and methods that enable the surgeon to secure such sling at such optimal tension/position relative the urethra. Moreover, the present invention is directed towards systems and methods for determining the position of and pressure within the urethra of the patient undergoing suburethral sling surgery and how such sling affects the optimal urethral positioning and the pressure such sling exerts thereabout.

In the first embodiment, the invention comprises the combination of a sensor for measuring tension and pressure and a monitor or meter coupled thereto. The sensor, which is preferably interposable between a suburethral sling and the urethra supported thereby, is specifically designed and configured to detect and quantify the pressure exerted by the sling against the urethra. In an alternative embodiment, the sensor is designed to measure the distance between the suburethral sling relative the urethra as may be desired in procedures that optimally place some degree of post-operative sag or slack in the suburethral sling. The monitor or meter coupled to the sensor provides a visual indication of the pressure that is being exerted by the sling upon the urethra, and/or alternatively, the spatial relationship of the sling relative the urethra, to thus enable the surgeon to manipulate and optimally position the sling. (i.e., set at tension levels and/or fixed distances and orientations from the urethra that correspond to statistical data indicative of favorable patient outcomes). In a further refinement, such meter additionally provides the surgeon with an indication as to when the sling pressure or placement has obtained ideal levels indicative of a favorable patient outcome so as to enable the surgeon to secure the sling in position in such a manner that an ideal pressure or urethral support is maintained.

In an alternative embodiment, the invention comprises a system and method for not only measuring and identifying the degree of tension in a suburethral sling and the amount of pressure exerted thereby upon the urethra, but further enables the surgeon to secure such sling to the patient at a position that maintains optimal support of the urethra. In such embodiment, the system comprises a tension monitoring device attached, via a suture line, to either a respective one or both ends of the sling as the sling is being surgically implanted within the patient. As with the first embodiment, the tension monitoring device measures and identifies the degree of tension placed on the sling, as well as when an optimal degree of tension is attained. However, such embodiment may further preferably be provided with a self-actuating locking member which locks the sutures in position and prevents further tension from being applied to the sling by the surgeon once an amount of sling tension/urethral support reaching a predetermined level that correlates with the best or most desirable results is attained. The device may further be optionally provided with means for detaching the suture connecting the sling with the device and securing the same to the abdominal fascia or pubic bone when a predetermined tension level is attained to thus secure the sling in a position that preserves the optimal post-operative urethral support. The device may further be designed to include a corrective mechanism that causes the sutures to be secured to the patient at decreased tension levels to ensure that such sling is maintained only in close proximity to the urethra and does not exert any pressure thereupon.

The present invention further comprises systems and methods for accurately determining the position of the urethra, and more particularly, the urethral angle, of a patient undergoing suburethral sling surgery. Such apparatus may further be modified to determine the amount of intra-urethral pressure of a patient undergoing such surgery. In the preferred embodiment, the invention comprises a probe member insertable within a portion of the urethra coupled to a monitor. The sensor member measures the urethral angle of the patient, as well as how the urethral angle changes as the tension in a suburethral sling is either increased or decreased. The sensor may further be adapted to measure intra-urethral pressure and how such pressure changes with increased or decreased tension in the suburethral sling.

The monitor coupled to the sensor provides the surgeon performing the operation with the data regarding the urethral angle and/or intra-urethral pressure so that the sling may be secured to the patient in a manner that optimizes the anatomical position of the urethra. Such embodiment may be used in other types of urologic and/or gynecologic surgical procedures, and further may be used either alone or in combination with the aforementioned tension monitoring devices to thus ensure that proper urethral positioning is attained as a result of such surgical procedure.

It is therefore an object of the present invention to provide a system and method for accurately measuring the tension in a suburethral sling, as well as the urethral support imparted thereby, to a surgeon during the performance of a suburethral sling surgical procedure.

Another object of the present invention is to provide a system and method for providing a surgeon performing a suburethral sling surgical procedure with an indication as to the degree of tension of the sling, as well as when such sling tension and urethral support imparted thereby have obtained optimal parameters for the patient undergoing such procedure.

Another object of the present invention is to provide a system and method for providing a surgeon performing a suburethral sling surgical procedure with an indication as to the spacing and orientation of the sling relative the urethra, as well as when such spacing between the urethra and sling have obtained optimal parameters for the patient undergoing such procedure.

Another object of the present invention is to provide a system and method for identifying and accurately setting the tension of a suburethral sling during the formation thereof in a suburethral sling surgical procedure, enable a surgeon to surgically secure a suburethral sling in a manner such that the sling is maintained at a desired tension or distance relative the urethra that optimally supports the urethra and minimizes post-operative complications following suburethral sling surgery.

Another object of the present invention is to provide a system and method for determining the position of the urethra, and more particularly, the urethral angle of the patient undergoing suburethral sling surgery to thus enable the physician to perform such surgery in a manner such that urethra is optimally positioned and supported by said sling.

Still further objects of the present invention include providing systems and methods for measuring and identifying the degree of tension in a suburethral sling, as well as indicate the support and position of the urethra that are of simple construction, easy to utilize, provide a high degree of accuracy, are inexpensive to deploy, and substantially minimize post-operative complications associated with suburethral sling surgery.

BRIEF DESCRIPTION OF THE DRAWINGS

These, as well as other features of the present invention will become more apparent upon reference to the drawings wherein:

FIG. 1 is a frontal-perspective view of the labia, vagina and catheterized urethra of a female patient placed in a dorsal lithotomy position with the labia being retracted laterally with sutures.

FIG. 2 is a perspective view of the anatomical structures depicting in FIG. 1, further depicting a sling member being passed through an incision formed upon the vagina and advanced therethrough, and passed around the urethra via a clamp, the latter having been advanced through an opening formed upon the patient's abdomen.

FIG. 3 is a perspective view of the sling depicted in FIG. 2 as positioned about the urethra wherein a respective one of the opposed ends of the sling is secured to the abdominal fascia. FIG. 3 further depicts a surgical monitor constructed in accordance to the preferred embodiment of the present invention, a sensor component thereof having been interposed between the sling and the urethra supported thereby.

FIG. 4 is a perspective view of the sling depicted in FIG. 2 as positioned about the urethra wherein a respective one of the opposed ends of the sling is secured to the abdominal fascia. FIG. 4 further depicts a surgical monitor constructed in accordance to a second preferred embodiment of the present invention, the latter of which being connected, via a suture, to the respective other opposed end of the sling to be secured to the abdominal fascia of the patient.

FIG. 4a is a perspective view of the device as depicted in FIG. 4 as utilized to secure the free end of a suburethral patch abdominal fascia once a particular tension in the patch is attained.

FIG. 5 is a cross-sectional view of a urethra, as supported by a suburethral sling. FIG. 5 further depicts a monitoring device for monitoring the urethral angle and/or intra-urethral pressure, of the urethra of a patient undergoing suburethral sling surgery.

DETAILED DESCRIPTION OF THE PREFERRED EMBODIMENTS

The detailed description as set forth below in connection with the appended drawings is intended as a description of the presently preferred embodiments of the invention, and is not intended to represent the only form in which the present invention may be constructed or utilized. The description sets forth the functions and sequences of steps for constructing and operating the invention in connection with the illustrated embodiments. It is understood, however, that the same or equivalent functions and sequences may be accomplished by different embodiments and that they are also intended to be encompassed within the scope of this invention.

Referring now to the drawings, initially to FIG. 1, there is prospectively depicted the pelvic region 10 of a female patient placed in a dorsal lithotomy position for purposes of undergoing a suburethral sling surgical procedure. The specifics regarding suburethral sling surgical procedures is described in detail in the references of Blaivas, Jerry G., *Successful Pubovaginal Sling Surgery, Contemporary Urology*, July, 1993; Blaivas, Jerry, G. *Treatment of Female Incontinence Secondary To Urethral Damage Or Loss*, Urologic Clinics of North America, Vol. 18, No. 2, May, 1991; Raz, Schlomo, *Surgical Therapy For Urinary Incontinence, Atlas Of Transvaginal Surgery*, W. B. Saunders, 1992, Loughlin, K. R., *The Endoscopic Fascial Sling Treatment of Female Urinary Stress Incontinence*, J. Urol, 1996, A.P.R.; 155 (4): 1265–7; and Staskin, D. R., et al., *The Gore-Text Sling Procedure For Female Sphincteric Incontinence: Indications, Technique And Results*, J. Urol, 1997; 15(5): 295–9, the teachings of which are expressly incorporated herein by reference.

As is recognized, such positioning provides the necessary access to the vagina to facilitate such access, the labia 14 is retracted laterally, typically by stay sutures 16. Similarly, a weighted postural vaginal retractor is incorporated to provide the surgeon with intravaginal access. Such surgical procedure further necessitates that a urethral catheter 18 be inserted within the urethra 20 during such surgical procedure.

With the patient in the lithotomy position as shown, an inverted U-shape 22 incision, as shown in FIG. 2, is made in the interior vaginal wall. The lateral edges of the resultant wound are thereafter retracted laterally to thus enable the surgeon to perform the necessary dissection that must be made to ultimately enable the surgeon to define a tunnel created toward the suprapubic area.

By forming an incision 24 upon the lower abdomen 26 of the patient, and more particularly an incision made just above the pubic bone, as depicted in FIG. 2, there is thus caused to be formed a continuous tunnel 28 extending from the suprapubic area through the retropubic space and out through the vaginal incision 22. At this stage of the procedure, a sling 30 may be introduced from the vaginal to suprapubic area, typically via a clamp 32, the latter extending through the tunnel 28 defined by the aforementioned surgical procedure. As is well known to those skilled in the art, the sling 30 may be comprised of synthetic materials or, alternatively, may comprise an elongate graft of tissue harvested from the patient or donor.

A respective one 30a of the opposed ends 30a, 30b of the sling 30 is attached to the abdominal fascia, pubic bone, or Cooper's Ligament, as shown in FIG. 3, thus fixing one side of the sling. The respective other free-end 30b of the sling 30 is then placed around all or a portion of the urethra 20, and may thereafter be secured by the surgeon to the other side of the abdominal fascia, pubic bone, or Cooper's Ligament.

However, as further depicted in FIG. 3, there is shown a surgical monitoring device 50 that is specifically designed to measure and provide an indication as to the degree of tension placed on the sling, as well as the pressure the sling exerts upon the urethra supported thereby. The surgical monitoring device 50 may likewise be adapted to provide an indication as to the distance or spatial relationship between a sling relative to the urethra. As is well known in the art, significant post-operative complications can arise as a result of the surgeon having placed too much tension on the sling, or placing the sling in too close proximity to the urethra, at the time of surgery. Such excess tension or poor sling placement has been shown to cause urinary retention, detrusor instability, or both. However, there is currently lacking in the art any systems or methods by which the tension or spatial orientation of such suburethral slings can be measured, let alone quantified in such a matter enables the surgeon to surgically secure such slings in position that optimizes urethral positioning or support and hence, optimizes the patient's outcome.

According to the first preferred method shown in FIG. 3, the surgical monitoring device 50 comprises a pressure or contact sensor 52 interposable between the sling 30 and the urethra 20 supported thereby. Such sensor 52, which may take the form of any a variety of those well known to those skilled in the art, is designed to measure either the spatial separation between the sling and the urethra and/or the compressive force exerted by the sling upon the urethra to generate a signal correspondingly thereto.

Although any of a number of sensors are known in the art and are commercially available that can readily identify and measure the distance and/or pressure exerted between the sling 30 and the urethra 20, it is contemplated that one embodiment may simply comprise the combination of a balloon coupled to a fluid-filled syringe (not shown). The balloon may preferably be pre-filled or, at the time of surgery, filled to a certain volume using the syringe to establish a baseline distance and/or pressure, before tension is applied to the sling. Thereafter, during the surgery when placement and tension in the sling 30 are being set, such sensor device can then measure the spatial separation and/or the compression of the sling upon the urethra as the sling is fixed or tied in place.

It should be understood, however, that the sensor 52 member need not be limited to applications where the same must necessarily be interposed between the urethra 20 and the sling 30, but may be affixed or positioned upon the sling 30 and/or urethra 20 at any point therealong, so long as the tension, pressure and/or spatial relationship between such structures can be sufficiently measured and identified by such sensor device 52. It is additionally contemplated that intra-urethral sensor devices for measuring intra-urethral pressure may further be utilized for quantifying such tension and/or pressure, such as those discussed further herein.

The sensor 52 is coupled, via cord 54, to a meter or monitor 50 that provides an indication as to the degree of tension and/or pressure being exerted by the sling 30 based upon signals received from the sensor 52. Such signals may likewise be utilized to correlate the spatial relationship between the sling and the urethra. For example, in the balloon embodiment discussed above, it is contemplated that internal pressure within the balloon can serve a basis for determining the spatial relationship between the sling and the urethra. Presently, it is contemplated that internal pressure may be quantatively measured as sling tension is proportionately increased or decreased. As a consequence, the sensor 52 may further be capable of providing an indication to monitor 50 of the spatial distance or separation between the urethra and the sling. For purposes of the present invention, it is further contemplated that in addition to indicating the spacing and/or degree of tension exerted by the sling 30, the devices of the present invention may further make a comparative analysis between the spacing and/or tension placed upon a given sling 30 and spacing and/or tension parameters that have been derived from a database of sling settings corresponding to sling spacing and/or tension levels that have ascertained from a determined patient population having undergone suburethral sling surgery and have had favorable outcomes.

In this regard, it is contemplated that the present invention may further incorporate the use of a microprocessor or signal processor (not shown) that processes the signal received from the sensor 52 and makes a comparison to such established tension parameters to thus provide the surgeon with an indication of not only what tension is placed upon the sling 30, but also whether such tension is indicative of a favorable post-operative outcome, namely, that the urethra will be sufficiently supported and that the sling will not secured to the patient with excessive or inadequate tension.

To derive such tension and/or pressure parameters, it is understood that it may be necessary to accumulate a statistically significant number of tension readings from a sufficiently large population of patients having undergone suburethral sling surgery before such tension parameters can be established. Alternatively, such tension and/or pressure parameters indicative of a favorable post-operative outcome may be determined based upon certain physiological characteristics of the patient undergoing surgery, or may even comprise simple threshold levels estimated to produce the desired post-operative outcome. Notwithstanding, once such tension parameters have been established, it is contemplated that the devices of the present invention will be capable of providing the surgeon with a signal when the tension is too high to thus enable the surgeon to take corrective measures by decreasing the tension in the sling prior to fixing the same in position.

Along these lines, it is contemplated that the sensor 52 may likewise be adapted to exclusively measure the distance or spacing between the urethra and the sling extending therebeneath. In this respect, and as opposed to measuring sling tension and urethral pressure exerted thereby, optimal sling placement may be predicated upon the sling having a desired degree of slack or sag, and hence, may not readily produce a measurable tension, let alone urethral pressure to be consequently produced thereby. In such applications, it is contemplated that such sensor 52 may take the form of an inflatable balloon, as discussed above, whereby the spatial distance between the urethra and sling may be measured as a function of either the volume in the balloon, or alternatively, the internal pressure within the balloon. Still further, it is contemplated that sensor 52 may take the form of a shim (not shown) that is interposable between the urethra and sling and capable of defining a relative spacing or distance when interposed therebetween.

As discussed above, it is further contemplated that in those cases where it is deemed desirable to introduce a fixed degree of sag or slack to a sling, desired sling spacings relative the urethra may be derived from statistical analysis of a sufficiently large population of post-operative patients having undergone suburethral sling surgery. Likewise, it is contemplated that certain individuals possessing certain physiological characteristics may fit certain known profiles that statistically warrant a particular spacing arrangement between a sling and the urethra that is most indicative of an optimal surgical outcome.

Along these lines, it should be recognized that much of the medical literature tends to indicate in a vast majority of patients, the sling 30 should be placed with little to no tension at all (and oftentimes with a relative degree of slack). Accordingly, in those patients undergoing suburethral sling surgery that may be optimally treated by forming slings having little or no tension at all, the devices of the present invention may further operate to provide an indication to the surgeon at the time of surgery as to when: 1) any appreciable tension is placed on the sling 30; 2) if the sling 30 just comes into contact with the urethra 20; or 3) what degree of slack or sag is present in a sling, as well as the fixed distance between the sling and the urethra. Such indications may be particularly useful for inexperienced surgeons unfamiliar with the procedure and, out of concern for the patient, inadvertently form and implant a sling 30 having improper placement and/or an excess of tension.

Referring now to FIG. 4, there is shown a second embodiment 60 of a surgical tension/pressure monitoring device constructed in accordance to the present invention. Such embodiment, similar to the first embodiment discussed above, is specifically designed and adapted to measure and identify the tension in a suburethral sling 30 as the same is fixed or tied in place during surgery. As illustrated, the device 60 comprises a tension monitor 62 that is affixed, via a suture, to a respective one of the opposed ends of the graft or sling being implanted to support the urethra.

In the particular embodiment shown, it will be recognized that such device 60 is deployed after the respective other end 30a of the graft or sling 30 has been fixed or tied in place. In this regard, it is known to those skilled in the art that the opposed ends 30a, 30b of the sling 30 may be either secured to the abdominal fascia, or alternatively, fixed to the pubic bone of the patient.

As the free-end 30b of the sling 30 is placed around all or a portion of the urethra 20, the sutures 64 stitched therethrough are pulled upwardly in the direction A such that measurable tension is created in the sling 30 that can be quantified to thus provide an indication to the surgeon when such tension has reached an optimal level based upon established or predetermined parameters. At such point, the sling 30 may be fixed or tied in place in such a manner that the ideal tension levels in the sling are preserved. In order to more accurately assess the resultant amount of the pressure the sling 30 exerts upon the urethra 20, it is presently contemplated that such tension monitoring device 60 will ideally be utilized in combination with the suburethral surgical tension/pressure monitor 50 depicted in FIG. 3 with the sensor member 52 thereof being interposed between the sling and the urethra while the free-end of the sling is pulled upwardly. In this regard, the device 60 affixed to the sutures 63 will be electrically coupled via connection 68 to monitor 56 such that tension/pressure levels measured by both the device 60 and sensor 52 can be concurrently evaluated.

In a further refinement of such embodiment, such tension monitoring device 60 may further be provided with a self-actuating locking member 70 that locks the sutures 64 into position once a predetermined pressure or tension is realized in the sling 30. Such embodiment may further be refined such that the sutures 64 are actually either fixed or tied in place to the abdominal fascia (e.g., via surgical staple) or fixed into the pubic bone to thus enable the surgeon to perform the suburethral sling surgery in a virtually error-free manner insofar as the surgeon will be prohibited from placing too much tension on the sling 30 at the time of surgery.

In an alternative embodiment 80 depicted in FIG. 4a, there may further be provided a surgical tension/pressure monitor 82 used in suburethral sling surgery that, as opposed to measuring the tension in a sling 30 from free-end 30b of a sling, which may take the form of a patch-type sling 31 as shown, placed around the ureterovesical junction, simultaneously measures the tension from both ends 31a, 31b of the sling 31 prior to when the same are fixed or tied to the abdominal fascia, pubic bone, or possibly to one another (i.e., the opposed ends of the sling themselves). In such embodiment 80, the device will measure the tension in the sling 31 when the sling 31 is placed around the urethrovesical junction with the opposed ends thereof extending through separate openings through the lower abdomen. The opposed ends of the sling 31a, 31b, which will be connected to the device via dedicated sutures 84, 86, enables the surgeon to place tension on the sling 31 by simply lifting the sutures 84, 86 in an upward direction through the lumen 88 of a manually operable tubular member 90 formed within the device.

Once the opposed ends of the sling 31a, 31b have been lifted or pulled a sufficient distance to create the desired tension in the sling 31, (i.e., via their dedicated suture connections extending within the device), the device 82 will then provide an indication to the surgeon that the ideal tension has been attained and to therefore affix the opposed urethral support ends of the sling to the patient so that such ideal tension may be maintained (e.g., a tension either selected by the surgeon or a tension corresponding to statistical data indicative of a favorable patient outcome). In this regard, similar to the embodiment depicted in FIG. 4, the device 84 will be coupled via a connection 92 to a monitor/display device 56.

In a further refinement (not shown), such device 82 may further be provided with a self-actuating locking members that lock the respective sutures 84, 86 stitched through the ends of the sling 31a, 31b into position, namely to either the abdominal facia, pubic bone, or even to one another, once the ideal tension in the sling is attained. Such device 82 may even have integrated therein a surgical stapler or other like device to enable the surgeon to surgically affix the opposed ends of the sling 31a, 31b in any protected manner known in the art.

It will further be appreciated by those skilled in the art that either of the tension monitors 62 and 82 depicted in FIGS. 4 and 4a may further be utilized simply as surgical fixation devices designed to secure the free end or ends of the sling 30, 31 in position when either a signal is received from a sensor, such as 52, or even self-actuate if merely a given threshold tension level in the sling 30 is achieved. Such devices 62, 82 may even be provided with a trigger mechanism (not shown) that enables the surgeon to actuate the self-actuating locking members on such devices so that the end or ends of the sling 30, 31 and/or the sutures affixed thereto, may be selectively fixed in position (or even tied to one another) at a specific site on or within the patient.

As per the first embodiment, it will be recognized that in either of the embodiments depicted in FIGS. 4 and 4a, that such devices may be designed to fix the sutures in position such that the sling does not exert any pressure upon the urethra, but is merely maintained at a fixed distance in close proximity thereto. In this regard, it is presently contemplated that a certain degree of slack could be maintained in the sutures during the point at which the same are secured to the patient. As a result, such sling, rather than exerting any pressure or deflection upon the urethra, merely enables the same to maintain its normal pre-operative position. When the patient makes provocative gestures, as occurs during coughing for example, the sling serves as a support floor that prevents incontinence occurring during such provocative event.

Referring now to FIG. 5, there is shown a urethral support monitoring device 100 that may be utilized alone or in combination with the aforementioned surgical tension/pressure monitoring devices to provide yet a further indication when a suburethral sling 30 provides an optimal degree of support to the urethra 20 supported thereby. As illustrated in the cross-sectional view, there is shown the lumen of a urethra 20 extending from bladder 102, as supported by a suburethral sling 30. As is known in the art, as the tension in the sling 30 increased or decreased, so does the urethral angle (i.e., the angle by which the urethra extends from the bladder to the anterior vaginal wall). The device 100 is specifically designed and configured to measure the urethral angle during suburethral sling surgery so that the sling 30 formed by the surgeon results in the urethra 20 attaining an optimal anatomical position. In this regard, it is considered by many that the urethral angle should be supported at approximately in order for the same to function optimally.

The device 100 comprises the combination of a probe 104 insertable within the urethra 20 or a portion thereof, that measures the urethral angle during sling surgery coupled with a monitoring apparatus. As the tension in the sling is adjusted to an optimal level, as may be determined by any of the aforementioned embodiments, the urethral angle formed as a result of the support provided by the sling 30 may be further determined to confirm that the sling 30 has been set at an optimal tension. In this regard, the probe 100 will produce a signal corresponding to the urethral angle that is then sent via connection 106 to the monitor 108, the latter providing the surgeon with a visual indicator or sound, which may take the form of a simple visual indicator that signals that the urethral angle is either been maintained within ideal parameters or, alternatively, that the urethra 20 is suboptimally positioned.

In an alternative embodiment 120 depicted in FIG. 5a, the probe 122 may, in addition to or separate from providing a measurement as to the urethral angle assumed by the urethra 20 during sling surgery, be adapted to measure intra-urethral pressure and produce a signal corresponding to the monitor 126 coupled therewith which thus produces a perceptible signal providing the surgeon with an indication as to the amount of pressure being exerted upon the lumen of the urethra 20, as well as how the intra-urethral pressure changes with the varying degrees of tension applied to the suburethral sling 30 or patch supported thereby.

In either of the embodiments depicted in FIGS. 5 and 5a, it will be recognized that the same may be adapted to sense the slightest pressure or movement within the urethra 20 such that a signal may be generated to indicate when there has been the slightest degree of contact between the sling 30 and the urethra 20. As discussed above, it is contemplated that it may be desirable to provide the surgeon with an indication when the sling 30 merely comes in close proximity, but does not exert any direct force upon the urethra 20 except in those instances where the urethra 20 is compressed against the sling when the individual performs a provocative motion.

Moreover, while it is intended that such probes 104, 122 and monitors 108, 126 respectively coupled therewith may be used in combination with the aforementioned sling tension/pressure monitoring devices depicted in FIGS. 3–4a, these specific embodiments 100, 120 may be used separate and independent therefrom. In this regard, such device 100, 120 may be used in connection with conventional suburethral sling surgery to thus provide an indication when the sling 30, as fixed into position by the surgeon, causes the urethra 20 supported thereby to maintain a desired urethral angle or intra-urethral pressure.

While it is intended that such probe and monitor coupled therewith may be used in combination with the aforementioned sling tension/pressure monitoring devices, such device may be used separate and independent from such devices. In this regard, such device may be used in connection with conventional suburethral sling surgery to thus provide an indication when the sling, as fixed into position by the surgeon, causes the urethra supported thereby to maintain a desired urethral angle or intra-urethral pressure.

Alternatively, such embodiments 100, 120 may be coupled with the other tension/pressure monitoring devices of the present invention and the data produced collectively thereby correlated with the tension/pressure data to thus provide the surgeon with a comprehensive indication of not only the tension and pressure that is being exerted by the sling 30 upon the urethra 20, but further indicates the consequential urethra angle and/or intra-urethral pressure that is caused thereby. The surgeon will thus be provided with means for incrementally adjusting the sling tension to a level to thus maintain the urethral angle and/or intra-urethral pressure at optimal positions and/or levels. For example, to the extent a 10% increase in sling tension corresponds to a 4° deviation in the urethral angle, a urethral angle that deviates by 12° would thus indicate that tension in the sling should be reduced by 30%, which could be easily achieved by the surgeon by adjusting tension in the sling until such 30% decrease in tension is achieved. Similarly, changes in sling tension can be correlated to correspond with incremental changes in intra-urethral pressure. For example, a 10% change in sling tension can be quantified to correspond to a 10 mm Hg change in intra-urethral pressure.

As discussed above, it will be recognized that certain parameters will be established regarding various levels and ranges of tensions that will provide the optimal degree of urethra support and that further minimize post-operative complications. To establish such parameters, whether such parameters are expressed in terms of ranges of infra-urethral pressure or radians of the urethral angle, it is contemplated that a sufficient number of suburethral sling surgical procedures might need to be performed upon a sufficient patient pool so that such parameters can be established, and will necessarily have to take into account such factors as age, ethnicity, medical history, prior surgeries, urethral pressure, among other important factors. However, it is believed that once a sufficient patient population upon which such surgical procedure has been performed there will consequently be derived preferred ranges of sling tension, urethral support and/or peri-operative urethral pressure that can be readily identified for a specific patient, and that the devices disclosed herein can be readily deployed and provide the surgeon with sufficient data to optimally perform such procedure.

Additional modifications and improvements of the present invention may also be apparent to those skilled in the art. Thus, the particular combination of the parts described and illustrated herein is intended to represent only one embodiment of the present invention, and is not intended to serve as limitations of alternative devices within the spirit and scope of the invention. Moreover, it should be understood that all of the embodiments disclosed herein may find use in a wide variety of urological and gynecologic surgical procedures other than the suburethral sling surgical procedures discussed herein. For example, it will be readily recognized that the specific embodiments depicted in FIGS. 5 and 5a may find wide spread use in urinary prosthesis implantation procedures. Accordingly, it is to be understood that the present invention is in no way to be deemed limited thereto.

What is claimed is:

1. A device for determining the spatial relationship between a suburethral sling and the urethra of a patient comprising:

a) a sensor interposable between said sling and said urethra, said sensor being designed to produce a signal corresponding to the position of said sling relative said urethra; and b) a monitor coupled to said sensor for receiving said signal generated thereby, said monitor being designed to provide a quantifiable indication of the relative positioning between said sling and said urethra.

2. The device of claim 1 further comprising:
   a) a signal processor coupled to said sensor and said monitor, said signal processor be designed to compare the signals generated from said sensor corresponding to the distance separating said sling from said urethra and compare said distance to establish spatial parameters such that a comparative indication of the distance between said sling and said urethra relative said established parameters is provided via said monitor.

3. The device of claim 2 wherein said established spatial parameters consist of a database of spatial settings that correspond to fixed distances between said sling and said urethra that have been ascertained from a determined patient population having undergone suburethral surgery.

4. The device of claim 1 wherein said sensor comprises a balloon member interposable between said urethra and said sling, said balloon being fluidly coupled to a volume indicating device such that in use, as said balloon expands and contracts, a signal is caused to be generated corresponding to the distance separating said urethra from said sling.

5. The device of claim 1 wherein said sensor comprises a balloon member having a sensor for determining the internal pressure thereof, said balloon member being interposable between said urethra and said sling such that in use, as said sling is caused to compress against said balloon, a signal indicative of internal pressure within the balloon is generated corresponding to the distance separating said urethra from said sling.

6. The device of claim 1 wherein said sensor comprises a shim member interposable between said urethra and said sling, said shim member being operative to generate a signal corresponding to the distance separating said urethra from said sling as said shim is extended therebetween.

7. A method for measuring and monitoring the amount of tension placed on a suburethral sling during the surgical or postoperative fixation thereof comprising the steps:
   a) providing a pressure sensor positionable upon said sling, said sensor being designed to produce a signal corresponding to the degree of tension placed on said sling during the surgical or postoperative fixation thereof;
   b) positioning said pressure sensor on said sling; and
   c) monitoring said signal generated by said pressure sensor on said sling.

8. The method of claim 7 wherein step a) further comprises providing a monitor, said monitor being coupled to said pressure sensor and operative to provide a quantifiable indication of the degree of tension placed upon said sling as indicated by said signal generated thereby.

9. The method of claim 7 wherein said method further comprises:
   a) comparing said tension monitored in step c) with established tension parameters such that a comparative indication of the tension in said sling and the tension of said established parameters may be determined.

10. The method of claim 7 wherein in step a), said sensor is interposable between said sling and urethra supported thereby.

11. The method of claim 10 wherein in step a), said sensor comprises a balloon member interposable between said urethra and said sling, said balloon being fluidly coupled to a pressure indicating device such that in use, when an increase in tension is placed upon said sling, said balloon is correspondingly caused to incrementally increase the internal pressure therein such that a signal is caused to be generated corresponding to the degree of pressure exerted upon the urethra by said sling.

12. A method for measuring and monitoring the distance between a suburethral sling and the urethra of a patient during the surgical or postoperative fixation thereof comprising:
   a) providing a sensor positionable upon said sling, said sensor being designed to produce a signal corresponding to the spatial relationship between said sling and said urethra during the surgical or postoperative fixation of said sling;
   b) positioning said sensor upon said sling; and
   c) monitoring said signal generated by said sensor.

13. The method of claim 12 wherein in step a) further comprises providing a signal processor coupled to said sensor and said monitor, said signal processor be designed to compare the signals generated from said sensor corresponding to the distance separating said sling from said urethra and comparing said distance to establish spatial parameters such that a comparative indication of the spacing between said sling and said urethra relative said established parameters is provided via said monitor.

14. The method of claim 11 wherein in step a), said sensor comprises a shim member indisposable between said urethra and said sling, said shim member being operative to produce a signal indicative of the distance separating said sling from said urethra as such shim member is interposed therebetween.

15. The method of claim 12 wherein in step a), said sensor comprises a balloon member interposable between said urethra and said sling, said balloon having an internal pressure sensor such that in use, when an increase in tension is placed upon said sling, said balloon is correspondingly caused to incrementally increase the internal pressure therein such that a signal is caused to be generated corresponding to the spatial relationship between said sling and said urethra.

* * * * *